United States Patent
Nakashima et al.

(10) Patent No.: US 11,766,918 B2
(45) Date of Patent: Sep. 26, 2023

(54) VEHICLE AIR-CONDITIONING DEVICE AND VEHICLE PROVIDED WITH VEHICLE AIR-CONDITIONING DEVICE

(71) Applicants: Panasonic Intellectual Property Management Co., Ltd., Osaka (JP); JAPAN CLIMATE SYSTEMS CORPORATION, Hiroshima (JP)

(72) Inventors: Yu Nakashima, Osaka (JP); Kou Komori, Nara (JP); Mio Furui, Osaka (JP); Kensaku Saitou, Tokyo (JP); Hiroshi Hamamoto, Hiroshima (JP); Yoichi Miyazaki, Hiroshima (JP); Hideaki Nishii, Hiroshima (JP); Hiroaki Shigenaka, Hiroshima (JP)

(73) Assignees: PANASONIC INTELLECTUAL PROPERTY MANAGEMENT CO., LTD., Osaka (JP); JAPAN CLIMATE SYSTEMS CORPORATION, Hiroshima (JP)

( * ) Notice: Subject to any disclaimer, the term of this patent is extended or adjusted under 35 U.S.C. 154(b) by 604 days.

(21) Appl. No.: 17/036,139

(22) Filed: Sep. 29, 2020

(65) Prior Publication Data
US 2021/0039471 A1 Feb. 11, 2021

Related U.S. Application Data

(63) Continuation of application No. PCT/JP2019/004903, filed on Feb. 12, 2019.

(30) Foreign Application Priority Data

Mar. 30, 2018 (JP) ................................. 2018-068774

(51) Int. Cl.
B60H 1/00 (2006.01)

(52) U.S. Cl.
CPC ..... *B60H 1/00742* (2013.01); *B60H 1/00892* (2013.01)

(58) Field of Classification Search
CPC .................. B60H 1/00892; B60H 1/00742
See application file for complete search history.

(56) References Cited

U.S. PATENT DOCUMENTS

| | | | | |
|---|---|---|---|---|
| 5,145,112 A | * | 9/1992 | Ueda | ........................ F24F 11/00 165/243 |
| 2009/0124926 A1 | * | 5/2009 | Funakura | ................. F24F 11/30 600/555 |

(Continued)

FOREIGN PATENT DOCUMENTS

| JP | 2009-132246 | 6/2009 |
|---|---|---|
| JP | 2011-024903 | 2/2011 |

(Continued)

OTHER PUBLICATIONS

Official Communication issued in International Patent Application No. PCT/JP2019/004903, dated May 7, 2019, along with English translation thereof.

*Primary Examiner* — Mohammad Ali
*Assistant Examiner* — Vincent W Chang
(74) *Attorney, Agent, or Firm* — Greenblum & Bernstein, P.L.C.

(57) ABSTRACT

A comfort sensation calculation unit quantitatively calculates comfort sensation of an occupant from an RRI of the occupant A, and a target control value of a thermal environment control device is set based on the comfort sensation of the occupant. Therefore, it is possible to achieve air conditioning control that reflects the comfort sensation of the occupant. When a signal output from the comfort sensation calculation unit and a signal output from the occupant thermal sensation calculation unit do not correspond to each (Continued)

other, the signal output from the comfort sensation calculation unit is corrected, and the target control value is determined.

7 Claims, 8 Drawing Sheets

(56) References Cited

U.S. PATENT DOCUMENTS

| | | | |
|---|---|---|---|
| 2018/0231269 A1* | 8/2018 | Hiei | G16H 40/63 |
| 2020/0352514 A1* | 11/2020 | Androulakis | F24F 11/65 |
| 2022/0268478 A1* | 8/2022 | Sudo | A61B 5/4266 |

FOREIGN PATENT DOCUMENTS

| | | |
|---|---|---|
| JP | 2011-246037 | 12/2011 |
| JP | 2012-147925 | 8/2012 |

* cited by examiner

VEHICLE AIR-CONDITIONING DEVICE AND VEHICLE PROVIDED WITH VEHICLE AIR-CONDITIONING DEVICE

CROSS-REFERENCE TO RELATED APPLICATIONS

This is a continuation of International Application No. PCT/JP2019/004903 filed on Feb. 12, 2019, which claims priority to Japanese Patent Application No. 2018-068774 filed on Mar. 30, 2018. The entire disclosures of these applications are incorporated by reference herein.

BACKGROUND

The present invention relates to, for example, a vehicle air conditioner provided for an automobile or any other vehicle and a vehicle including the vehicle air conditioner, and more particularly belongs to the technical field of means for detecting biosignals of an occupant.

Traditional vehicle air conditioners, in general, are configured to be capable of performing so-called automatic air conditioning control which automatically sets the temperature and the volume of air blown into the cabin, according to a predetermined algorithm using detected results of the interior temperature of the cabin, the outside air temperature, an amount of solar radiation, the temperature set by an occupant, and the like (see for example, Japanese Unexamined Patent Publication Nos. 2009-132246 and 2011-246037).

The air conditioner of Japanese Unexamined Patent Publication No. 2009-132246 is configured to measure a pulse wave signal of an occupant, estimate an individual characteristic based on the feature amount extracted from the pulse wave signal, and vary the control with respect to the set temperature in accordance with the estimated individual characteristic. The individual characteristic is a pulse wave transit time, a pulse wave waveform, an acceleration pulse wave, a cross-correlation coefficient of blood pressures and heart rates, variation in the fluctuation of the heart rate, and the like, and the control is varied by using such an individual characteristic to achieve health-considering air conditioning.

The air conditioner of Japanese Unexamined Patent Publication No. 2011-246037 is configured to detect a pulse wave of an occupant through a portable device carried by the occupant, calculate a numerical value co-related to coldness/hotness sensation of the occupant based on the detected pulse wave, cool the cabin if the numerical value indicates that the occupant feels hot, and warm the cabin if the occupant feels cold.

Further, Japanese Unexamined Patent Publication No. 2011-24903 discloses a technology that detects an electrocardiogram waveform of a driver by an electrode attached to a steering wheel of a vehicle while detecting vibration noise of the vehicle, and that obtains the electrocardiogram waveform of the occupant by subtracting the vibration noise from the electrocardiogram waveform detected by the electrode.

Further, Japanese Unexamined Patent Publication No. 2012-147925 discloses a biological information detection device that applies light to an occupant seated on a vehicle seat, receives reflected light from the occupant, and detects a pulse wave of the occupant based on changes in the amount of reflected light having been received.

SUMMARY

Traditional vehicle air conditioners in general are not able to find out whether an occupant is feeling cold or hot, and the air conditioning control is performed only on the basis of indirect information such as the temperature of the cabin and the like, without knowing the level of coldness or hotness the occupant feels. Therefore, the accuracy of the air conditioning control is not high, leaving some room for improvement.

An approach to address this issue is to measure the skin temperature of the occupant by, for example, using an infrared sensor, and perform air conditioning control based on the skin temperature. However, since there is a large individual difference in the skin temperature of occupants and the infrared sensor only obtains the temperature of the surface layer, this may not properly reflect the thermal sensation of the occupant. As a result, using the skin temperature of the occupant for air conditioning control may not improve the accuracy of the air conditioning control.

Another conceivable approach is to obtain the pulse wave of the occupant and perform air conditioning control based on the pulse wave obtained, as is disclosed in Japanese Unexamined Patent Publication No. 2009-132246. However, the disclosure of Japanese Unexamined Patent Publication No. 2009-132246 concerns changing of the air conditioning control in consideration of the health by using individual characteristic, rather than improving the accuracy of the air conditioning control. Furthermore, to detect the pulse wave of the occupant, there is a method disclosed in Japanese Unexamined Patent Publication No. 2011-24903, for example. However, the detected signals may contain a noise component, particularly the one attributed to vibration during traveling of the vehicle, and the noise may increase over time. Therefore, there is a problem in improving the air conditioning accuracy with this approach. The similar problem will apply to a case of detecting the pulse wave based on the amount of light received as disclosed in Japanese Unexamined Patent Publication No. 2012-147925.

With the portable device of Japanese Unexamined Patent Publication No. 2011-246037 that can be carried outside the cabin, it is possible to detect a pulse wave signal of the occupant without the noise attributed to vibration while the vehicle is traveling. However, the technology of Japanese Unexamined Patent Publication No. 2011-246037 is for so-called pre-air-conditioning, which is air conditioning before the occupant gets on the vehicle, and therefore, the above-described problem of noise takes place at a time of detecting the pulse wave of the occupant while the vehicle is traveling.

In view of the foregoing background, it is an object of the present invention to further improve the accuracy of air conditioning control by utilizing a pulse wave of an occupant.

To achieve the above objects, a vehicle air conditioner according to a first aspect of the present invention is a vehicle air conditioner mounted on a vehicle, the vehicle air conditioner including: a thermal environment detector configured to detect a thermal environment around an occupant in a cabin; an RRI detector configured to detect an RRI from a pulse wave of the occupant; a comfort sensation calculator configured to quantitatively calculate comfort sensation of the occupant from the RRI detected by the RRI detector, and output a signal indicating the comfort sensation of the occupant; a thermal environment control device configured to control the thermal environment around the occupant; a target control value setter configured to set a target control value of the thermal environment control device, based on the signal output from the comfort sensation calculator, which indicates the comfort sensation of the occupant; and an occupant thermal sensation calculator configured to obtain a thermal model of the occupant based on thermal sensation calculation information containing the thermal environment around the occupant which is detected by the thermal environment detector and an operation state of the thermal environment control device, quantitatively calculate thermal sensation of the occupant, and output a signal indicating the calculated thermal sensation, wherein the target control value setter is configured to determine whether the signal from the comfort sensation calculator and the signal from the occupant thermal sensation calculator correspond to each other, and execute a process of correction for the signal output from the comfort sensation calculator when both of the signals do not correspond to each other.

With this configuration, the comfort sensation of the occupant is quantitatively calculated from the RRI of the pulse wave of the occupant and a signal indicating the comfort sensation of the occupant is output from the comfort sensation calculator. The RRI is well known to vary due to the presence or absence of stress. For example, the RRI is shortened if a person feels stressed and is uncomfortable, while the RRI becomes longer when the person is relaxed and comfortable. Therefore, the comfort sensation of an occupant can be quantitatively calculated based on variation in the RRI.

Meanwhile, the thermal sensation of the occupant is quantitatively calculated based on the thermal sensation calculation information, and a signal indicating the thermal sensation of the occupant is output from the occupant thermal sensation calculator. The thermal sensation calculation information contains information of the thermal environment around the occupant and information of the operation state of the thermal environment control device. For example, when the temperature is low around the occupant, it is assumed that the occupant feels cold. On the other hand, when the temperature is high around the occupant, it is assumed that the occupant feels warm. Further, when the operation state of the thermal environment control device is in a strong heating state, it is assumed that the temperature in the cabin is low, and the occupant feels cold.

Then, since the target control value setter sets a target control value based on the comfort sensation of the occupant calculated by the comfort sensation calculator, the thermal environment control device controls the thermal environment around the occupant in the cabin so that the occupant feels comfortable. Therefore, air conditioning control reflecting the comfort sensation of the occupant is achieved and the accuracy of air conditioning control is improved.

Here, there could be a case in which the reliability of RRI obtained from the pulse wave of the occupant is low, particularly due to vibration or the like while the vehicle is traveling. In such a case, it is unlikely that the comfort sensation of the occupant calculated by the comfort sensation calculator reflects the actual comfort sensation of the occupant. Therefore, the target control value setter determines that the comfort sensation of the occupant calculated by the comfort sensation calculator and the thermal sensation of the occupant calculated by the occupant thermal sensation calculator do not correspond to each other. Then, since the target control value setter corrects the signal output from the comfort sensation calculator, the thermal environment around the occupant can be controlled without impairment of the comfort of the occupant.

In the vehicle air conditioner of a second aspect of the present invention, the target control value setter is configured to disable the process of correction when it is determined that the signal output from the comfort sensation calculator and the signal output from the occupant thermal sensation calculator correspond to each other.

With this configuration, the signal output from the comfort sensation calculator is not corrected if the RRI is properly detected from the pulse wave of the occupant. Therefore, the comfort sensation of the occupant is reliably reflected in the control of the thermal environment.

The vehicle air conditioner according to a third aspect of the invention includes a skin temperature detector configured to detect a skin temperature of the occupant, and the thermal sensation calculation information contains the skin temperature of the occupant detected by the skin temperature detector.

That is, the skin temperature of the occupant may represent the thermal sensation of the occupant, and by having information of the skin temperature contained in the thermal sensation calculation information, the accuracy of calculating the thermal sensation of the occupant can be improved.

In the vehicle air conditioner according to a fourth aspect of the invention, the comfort sensation calculator is configured to obtain the thermal environment around the occupant detected by the thermal environment detector and the operation state of the thermal environment control device, and when the RRI detected by the RRI detector changes although the thermal environment around the occupant and the operation state are not changed, calculate the comfort sensation of the occupant based on the RRI before the change.

That is, the RRI may change due to a stress on the occupant A, i.e., due to a factor other than the thermal sensation. In the present invention, when the RRI changes even though there is no change in the thermal environment around the occupant and the operation state, it is estimated that the RRI has changed due to a factor other than the thermal sensation, and the comfort sensation of the occupant is calculated from the RRI before the change. Therefore, the accuracy of calculating the comfort sensation of the occupant is improved.

In the vehicle air conditioner according to a fifth aspect of the invention, the comfort sensation calculator is configured to obtain the thermal environment around the occupant detected by the thermal environment detector, the operation state of the thermal environment control device, and the skin temperature detected by the skin temperature detector, and when the RRI detected by the RRI detector changes although the thermal environment around the occupant, the operation state, and the skin temperature of the occupant are not changed, calculate the comfort sensation of the occupant based on the RRI before the change.

In this configuration, when the RRI changes even though there is no change in the thermal environment around the occupant, the operation state, and the skin temperature, it is estimated that the RRI has changed due to a factor other than the thermal sensation, and the comfort sensation of the occupant is calculated from the RRI before the change. Therefore, the accuracy of calculating the comfort sensation of the occupant is improved.

In the vehicle air conditioner according to a sixth aspect of the invention, when the RRI cannot be detected by the RRI detector, the comfort sensation calculator calculates the comfort sensation of the occupant based on the signal output from the occupant thermal sensation calculator.

In this configuration, the thermal environment around the occupant can be controlled based on the thermal sensation of the occupant, when the RRI is not detected.

A vehicle including the vehicle air conditioner according to any one of the first to sixth aspects may be configured.

With the present invention, a comfort sensation calculator quantitatively calculates comfort sensation of an occupant from an RRI of the occupant A, and a target control value of a thermal environment control device is set based on the comfort sensation of the occupant. Therefore, it is possible to achieve air conditioning control that reflects the comfort sensation of the occupant, and improve the accuracy of the air conditioning control. Since the signal output from the comfort sensation calculator is corrected when the reliability of RRI of the occupant is low, the thermal environment around the occupant can be controlled without impairment of the comfort of the occupant.

DETAILED DESCRIPTION

An embodiment of the present invention will now be described in detail with reference to the drawings. The following description of preferred embodiments is only an example in nature, and is not intended to limit the scope, applications or use of the present invention.

(Configuration of Automobile 1)

Figure 1:
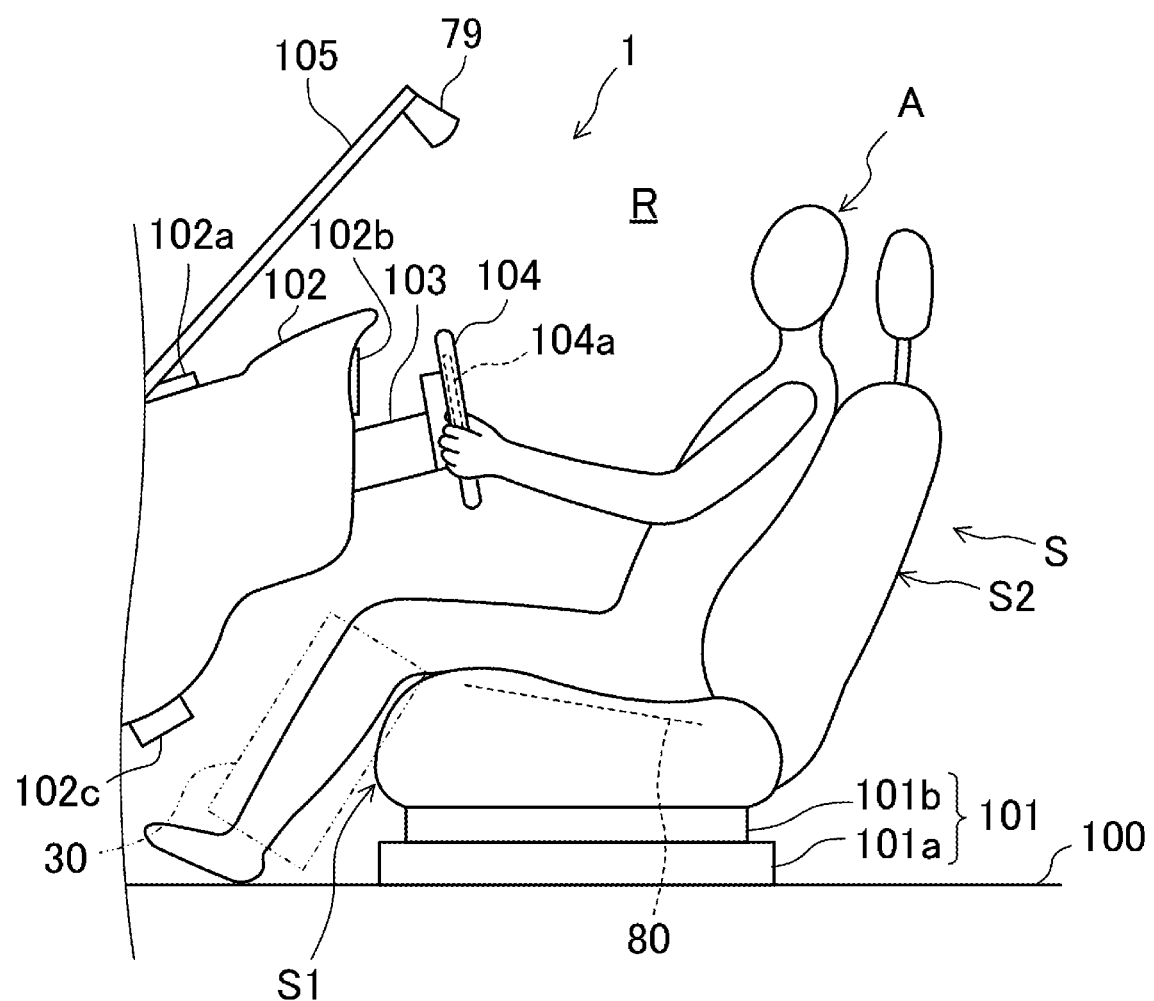
FIG. 1 is a side view illustrating a portion of the inside of the cabin of an automobile according to an embodiment of the present invention.

FIG. 1 is a side view of a portion of the inside of the cabin R of an automobile 1 according to an embodiment of the present invention. In the following description, the terms "front," "forward," and derivatives thereof refer to the front side of a vehicle in the longitudinal direction of the vehicle, the terms "rear," "rearward," and derivatives thereof refer to the rear side of the vehicle in the longitudinal direction of the vehicle, the terms "left," "leftward," and derivatives thereof refer to the left side of the vehicle in the lateral direction of the vehicle, and the terms "right," "rightward," and derivatives thereof refer to the right side of the vehicle in the lateral direction of the vehicle.

A vehicle seat S is attached to a floor panel 100 inside the cabin R with a sliding device 101 interposed therebetween. A front end portion of the cabin R includes an instrument panel 102 including instruments (not shown). A steering column 103 is provided on a portion of the instrument panel 102 near the driver's seat to protrude rearward. A rear end portion of the steering column 103 is provided with a steering wheel 104 facing an occupant A.

The sliding device 101 includes a rail member 101a fixed to the floor panel 100 and extending in the longitudinal direction, a guided member 101b fixed to a lower portion of the vehicle seat S and guided in the longitudinal direction by the rail member 101a, and a lock member (not shown) fixing the guided member 101b to the rail member 101a at a desired position.

The front end portion of the cabin R is provided with a windshield glass 105. A lower end portion of the windshield glass 105 is located near the front end of the instrument panel 102.

A front end portion of an upper surface of the instrument panel 102 has a defroster outlet 102a. The defroster outlet 102a faces the inner surface of the windshield glass 105, and extends over a predetermined area in the lateral direction. The defroster outlet 102a is an opening for allowing air-conditioned wind to blow toward the inner surface of the windshield glass 105 therethrough. A rear portion of the instrument panel 102 has vent outlets 102b for allowing air-conditioned wind to blow toward a portion of the upper body or the entire upper body of the occupant A. The vent outlets 102b are respectively formed on both right and left sides of the instrument panel 102 and a central portion thereof in the lateral direction, and face the driver and the occupant next to the driver. A lower portion of the instrument panel 102 has heat outlets 102c for allowing air-conditioned wind to blow toward a portion of the lower body or the entire lower body of the occupant A. The respective heat outlets 102c can open near the feet of the driver and the occupant next to the driver, and can be referred to also as "foot-side outlets." Although not shown, vent outlets and heat outlets may be provided not only for front-seat occupants but also for rear-seat occupants.

Figure 2:
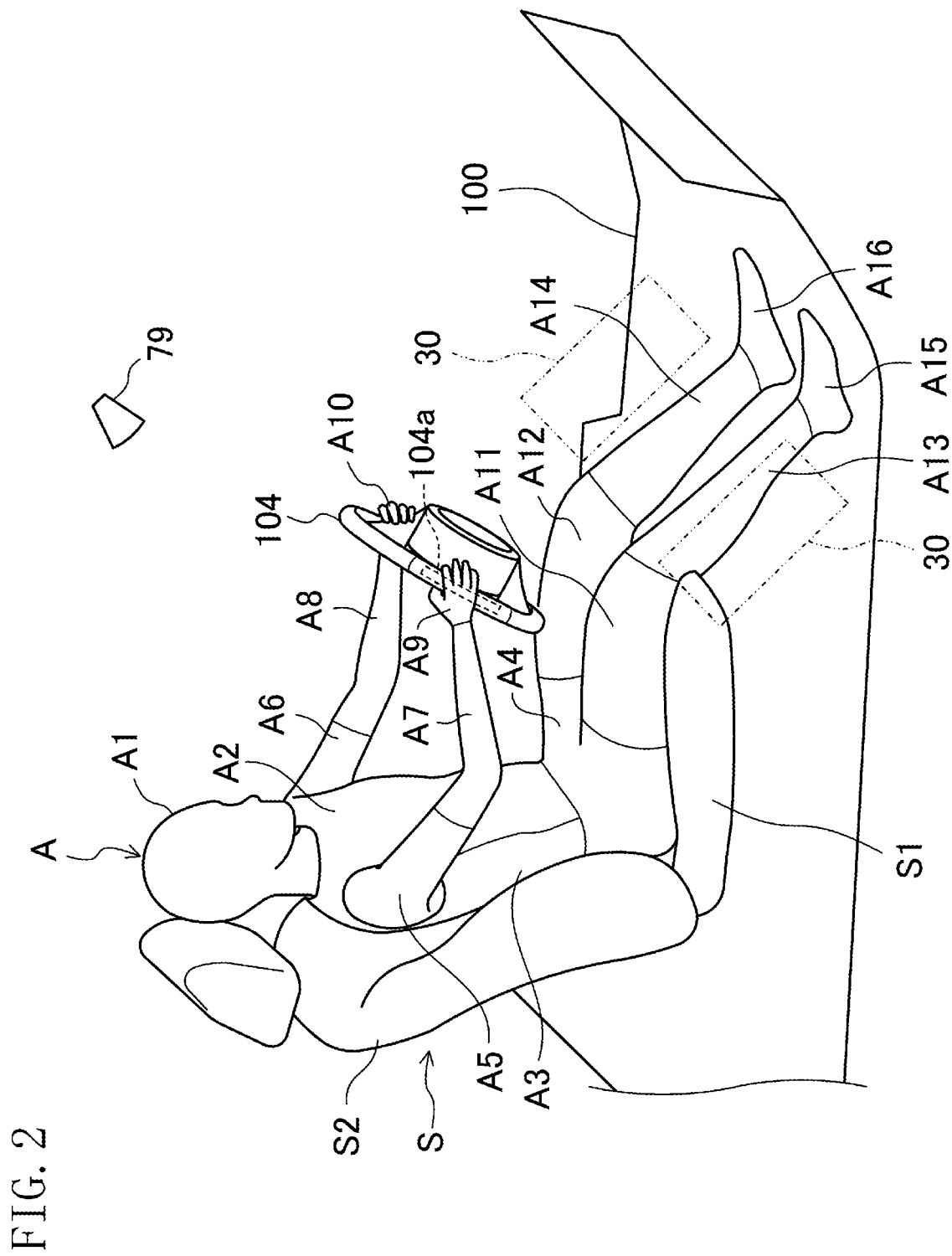
FIG. 2 is a perspective view illustrating a portion of the cabin near the driver's seat.
Figure 3:
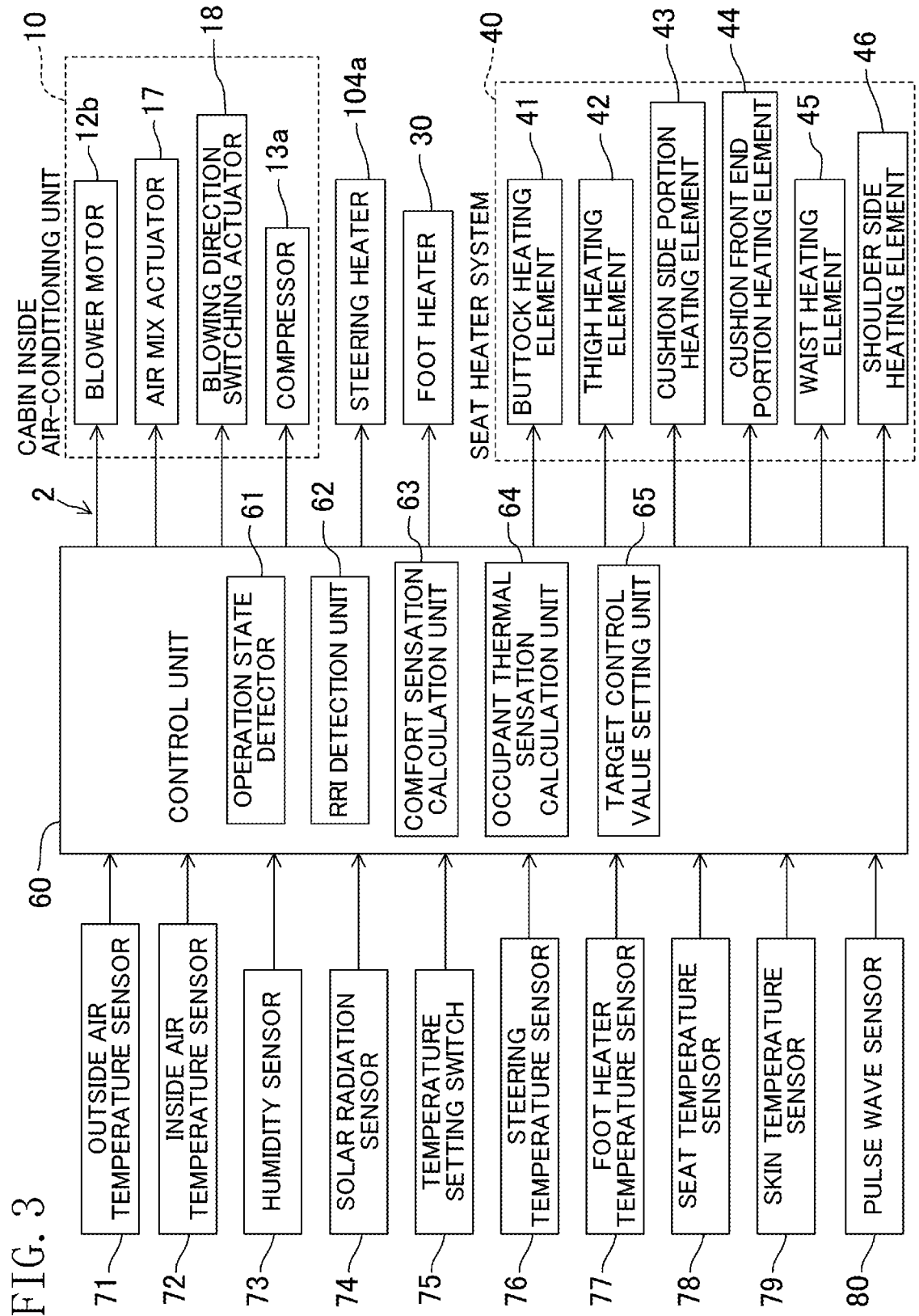
FIG. 3 is a block diagram of a vehicle air conditioner.

The automobile 1 includes a vehicle air conditioner 2 shown in the block diagram of FIG. 3. The vehicle air conditioner 2 includes, as a thermal environment control device, a cabin air-conditioning unit 10 (shown in FIG. 4), steering heaters 104a (shown in FIGS. 1 and 2), a foot heater 30 (shown in FIGS. 1 and 2), a seat heater system 40 (shown in FIG. 5), and a control unit 60 (shown in FIG. 3).

Note that the automobile 1 may be a passenger car, or may be a loaded vehicle, such as a truck. These are exemplary vehicles, and a vehicle other than an automobile may be equipped with the vehicle air conditioner 2.

(Configuration of Cabin Air-Conditioning Unit 10)

Figure 4:
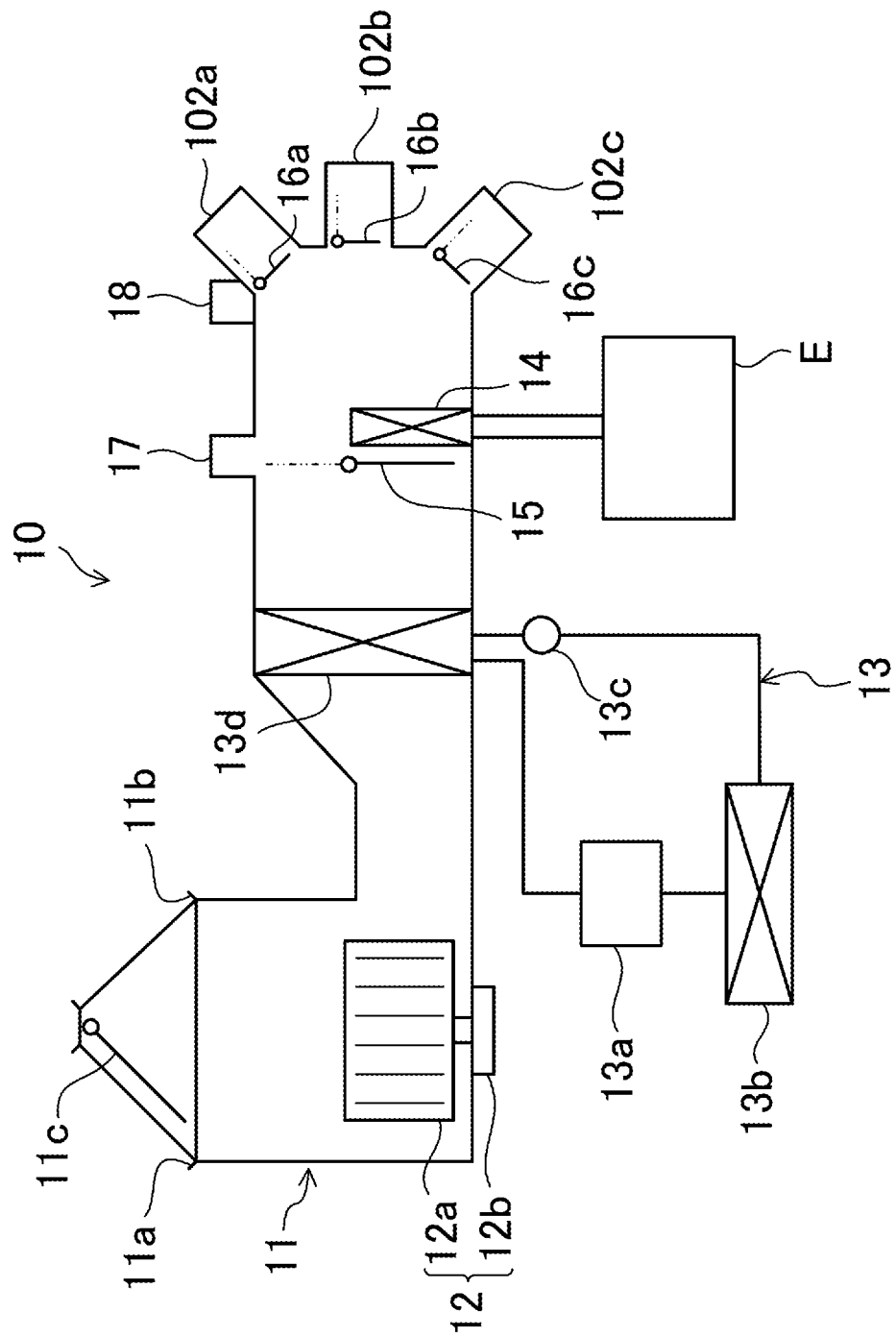
FIG. 4 is a schematic diagram of a configuration of a cabin air-conditioning unit.

The cabin air-conditioning unit 10 is configured to produce air-conditioned wind blowing out of the defroster outlet 102a, the vent outlets 102b, and the heat outlets 102c in the cabin R, and to control air conditioning in the cabin R, i.e., a thermal environment around the occupant A in the cabin R, using the air-conditioned wind. Specifically, as shown in FIG. 4, the cabin air-conditioning unit 10 includes an air-conditioning casing 11, a blower 12, a refrigeration-cycle system 13, a heater core 14, an air mixing damper 15, blowing direction switching dampers 16a, 16b, and 16c, an air mix actuator 17, and a blowing direction switching actuator 18.

The air-conditioning casing 11 has an inside air inlet 11a which communicates with the cabin R and through which air (inside air) in the cabin R is taken in the air-conditioning casing 11, and an outside air inlet 11b which communicates with the outside of the cabin R and through which air (outside air) outside the cabin is taken in the air-conditioning casing 11. The air-conditioning casing 11 includes therein an inside/outside air switching damper 11c operating to close one of the inside air inlet 11a or the outside air inlet 11b and open the other one of these inlets. If the inside/outside air switching damper 11c operates to open the inside air inlet 11a and to close the outside air inlet 11b, an operation is performed in an inside-air circulation mode. On the other hand, if the inside/outside air switching damper 11c operates to close the inside air inlet 11a and to open the outside air inlet 11b, an operation is performed in an outside-air introduction mode. The occupant A may manually switch the operation mode between the inside-air circulation mode and the outside-air introduction mode. Alternatively, a control unit 60 described below may automatically switch the operation mode therebetween.

The blower 12 includes a sirocco fan (centrifugal fan) 12a disposed inside the air-conditioning casing 11, and a blower motor 12b that rotationally drives the sirocco fan 12a. The sirocco fan 12a rotationally driven by the blower motor 12b allows air-conditioning air to be taken in the air-conditioning casing 11 through the inside air inlet 11a or the outside air inlet 11b. The air-conditioning air taken in the air-conditioning casing 11 is delivered toward the downstream side of the air-conditioning casing 11. Note that the type of blower 12 is merely an example. The blower 12 may be a blower including a fan except a centrifugal fan.

As shown in FIG. 3, the blower motor 12b is connected to the control unit 60. The control unit 60 turns the blower motor 12b on and off, and changes the rotational speed of the blower motor 12b per unit time. Increasing the rotational speed of the blower motor 12b per unit time increases the volume of air delivered by the blower 12.

As shown in FIG. 4, the refrigeration-cycle system 13 includes a compressor 13a, a condenser 13b, an expansion valve 13c, and an evaporator 13d, which are connected together through refrigerant pipes to allow a refrigerant to circulate therethrough. The compressor 13a is driven by an engine E (shown only in FIG. 4). A clutch (not shown) of the compressor 13 is controlled by the control unit 60 shown in FIG. 3. Thus, the compressor 13 is turned on and off.

The refrigerant discharged from the compressor 13a flows into the condenser 13b, and is condensed inside the condenser 13b. Then, the condensed refrigerant flows into the expansion valve 13c. The refrigerant that has flowed into the expansion valve 13c is decompressed, and then flows into the evaporator 13d. The evaporator 13d is disposed inside the air-conditioning casing 11, and the whole quantity of the air-conditioning air introduced into the air-conditioning casing 11 passes through the evaporator 13d. The refrigerant that has flowed into the evaporator 13d exchanges heat with the air-conditioning air passing through the outside of the evaporator 13d, while flowing through the inside of the evaporator 13d. Thus, the air-conditioning air is cooled, thereby producing cold air.

The heater core 14 is disposed downstream of the evaporator 13d in the airflow direction inside the air-conditioning casing 11. The heater core 14 is connected to a water jacket (not shown) of the engine E. A coolant in the engine E circulates through the heater core 14. Thus, if the coolant in the engine E has a higher temperature than the air-conditioning air passing through the outside of the heater core 14, the air-conditioning air is heated by exchanging heat with the coolant, thereby producing warm air.

Although not shown, in the case of an electric vehicle, for example, a coolant in a drive motor or an inverter can be passed through the heater core 14. Further, for example, in the case of an electric vehicle, the heater core 14 may be replaced with a heat pump system including an electric compressor 13a, and a refrigerant condenser (heating heat exchanger) may be provided inside the air-conditioning casing 11. In addition to the heater core 14, an electric heater (e.g., a PTC heater) or any other heater may be provided.

The air mixing damper 15 is a member for changing the ratio between the amount of air passing through the heater core 14 and the amount of air bypassing the heater core 14. As indicated by the solid line in FIG. 4, if the air mixing damper 15 fully closes a passage near the heater core 14, and fully opens a passage bypassing the heater core 14, air that has passed through the evaporator 13d does not pass through the heater core 14, and is thus fully cold. On the other hand, as indicated by the phantom line in FIG. 4, if the air mixing damper 15 fully opens the passage near the heater core 14, and fully closes the passage bypassing the heater core 14, the whole quantity of air that has passed through the evaporator 13d passes through the heater core 14, and is thus fully hot. The air mixing damper 15 can be stopped at an optional position between the position indicated by the solid line in FIG. 4 and the position indicated by the phantom line therein. Changing the position at which the air mixing damper 15 stops triggers a change in the ratio between the amount of air passing through the heater core 14 and the amount of air bypassing the heater core 14. As a result, the temperature of the produced air-conditioned wind is changed.

The air mix actuator 17 functions to actuate the air mixing damper 15, and is connected to the control unit 60 as shown in FIG. 3. The air mix actuator 17 can stop the air mixing damper 15 at a desired position upon receipt of a control signal from the control unit 60.

The blowing direction switching dampers 16a, 16b, and 16c shown in FIG. 4 are dampers for switching the direction in which air-conditioned wind blows out. One of the blowing direction switching dampers denoted by the reference character 16a is a damper for opening and closing the defroster outlet 102a, i.e., a defroster damper. Other ones of the blowing direction switching dampers denoted by the reference character 16b are dampers for opening and closing the vent outlets 102b, i.e., vent dampers. The other ones of the blowing direction switching dampers denoted by the reference character 16c are dampers for opening and closing the heat outlets 102c, i.e., heat dampers. The closed and open positions of each of the blowing direction switching dampers 16a, 16b, and 16c are indicated by the solid line and the phantom line, respectively. The blowing direction switching dampers 16a, 16b, and 16c can be stopped at an optional position between the closed position and the open position. Such motions of the blowing direction switching dampers 16a, 16b, and 16c can be achieved by a linkage (not shown) that has been known in the art.

The blowing direction switching dampers 16a, 16b, and 16c interlock with one another via the linkage to be capable of changing the direction in which air-conditioned wind blows out. For example, if the blowing direction switching damper 16a is in the open position, and the blowing direction switching dampers 16b and 16c are in the closed position, an operation is performed in a defroster mode in which air-conditioned wind blows out of only the defroster outlet 102a. If the blowing direction switching dampers 16b are in the open position, and the blowing direction switching dampers 16a and 16c are in the closed position, an operation is performed in a vent mode in which air-conditioned wind blows out of only the vent outlets 102b. If the blowing direction switching dampers 16c are in the open position, and the blowing direction switching dampers 16a and 16b are in the closed position, an operation is performed in a heat mode in which air-conditioned wind blows out of only the heat outlets 102c. If the blowing direction switching dampers 16a and 16c are in the open position, and the blowing direction switching dampers 16b are in the closed position, an operation is performed in a defrost/heat mode in which air-conditioned wind blows out of the defroster outlet 102a and the heat outlets 102c. If the blowing direction switching dampers 16b and 16c are in the open position, and the blowing direction switching damper 16a is in the closed position, an operation is performed in a bi-level mode in which air-conditioned wind blows out of the vent outlets 102*b* and the heat outlets 102*c*. The blowing modes described above are examples. Switching the blowing direction switching dampers 16*a*, 16*b*, and 16*c* between the open and closed positions allows switching to be made among the various modes, and triggers a change in the degree of opening of each of the defroster outlet 102*a*, the vent outlets 102*b*, and the heat outlets 102*c*. Thus, the volume of air-conditioned wind blowing out of each outlet can be changed.

The configurations of the blowing direction switching dampers 16*a*, 16*b*, and 16*c* are merely examples. For example, two dampers may also be combined together to switch the operation among the blowing modes.

The blowing direction switching actuator 18 functions to actuate the blowing direction switching dampers 16*a*, 16*b*, and 16*c*, and is connected to the control unit 60 as shown in FIG. 3. The blowing direction switching actuator 18 can stop the blowing direction switching dampers 16*a*, 16*b*, and 16*c* at respective desired positions upon receipt of a control signal from the control unit 60. Thus, an operation can be performed in any one of the blowing modes described above.

(Configuration of Seat Heater System 40)

Figure 5:
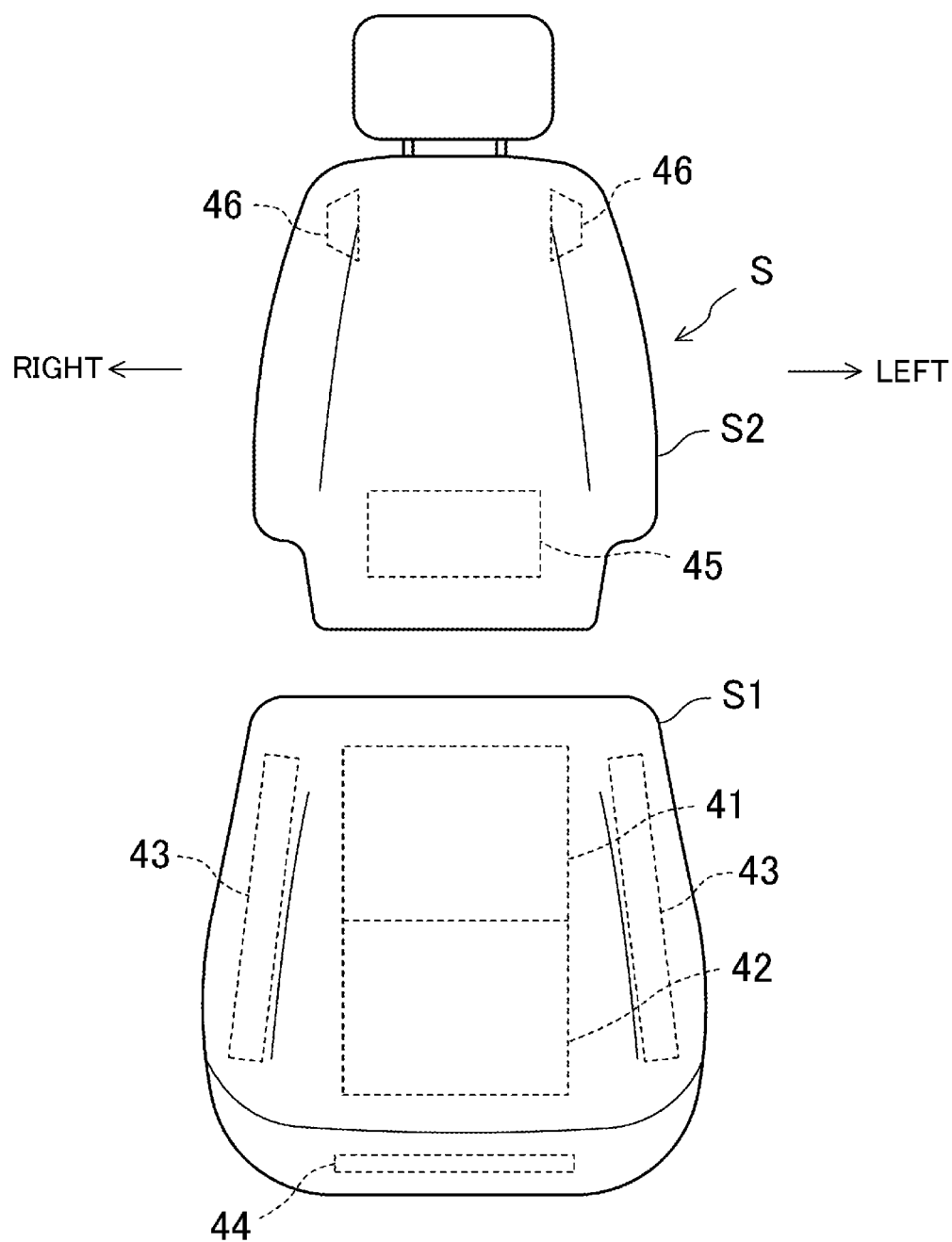
FIG. 5 illustrates a state in which a vehicle seat including a seat heater is divided into a seat cushion part and a seat back part.

As shown in FIG. 5, the seat heater system 40 is incorporated into the vehicle seat S. The vehicle seat S includes the seat cushion part S1, and the seat back part S2. FIG. 5 illustrates a state in which the vehicle seat S is divided into the seat cushion part S1 and the seat back part S2 for convenience of description. As shown in FIGS. 1 and 2, when the vehicle seat S is installed in the vehicle 1, the seat cushion part S1 and the seat back part S2 are integrated together. The vehicle seat S described in this embodiment constitutes a driver's seat. However, the present invention is applicable also to a seat constituting a seat next to the driver or a seat constituting a rear seat. The present invention is applicable also to a so-called bench seat on which a plurality of people can be seated side by side in the lateral direction.

The vehicle seat S includes the seat cushion part S1, and the seat back part S2. The seat cushion part S1 may be referred to also as a "seat bottom part," and is configured to mainly support, from below, a portion of the occupant A from his/her buttocks (bottom) to his/her thighs. The seat back part S2 may be referred to also as a "seat backrest part," and is configured to mainly support, from behind, the waist and back of the occupant A, portions of the occupant A around his/her shoulder blades, and his/her shoulders.

The seat heater system 40 includes a buttock heating element 41, a thigh heating element 42, cushion side portion heating elements 43, a cushion front end portion heating element 44, a waist heating element 45, and shoulder side heating elements 46. The buttock heating element 41, the thigh heating element 42, the cushion side portion heating elements 43, and the cushion front end portion heating element 44 are incorporated into the seat cushion part S1, and can be specifically disposed between a cushion material and an external skin material. The buttock heating element 41, the thigh heating element 42, the cushion side portion heating elements 43, and the cushion front end portion heating element 44 are connected to, and controlled by, the control unit 60.

The waist heating element 45 and the shoulder side heating elements 46 are incorporated into the seat back part S2, and can be specifically disposed between a cushion material and an external skin material. The waist heating element 45 and the shoulder side heating elements 46 are connected to, and controlled by, the control unit 60.

Each of the heating elements 41 to 46 is configured as, for example, a wire rod that generates Joule heat by energization. Specifically, each heating element according to this embodiment uses the phenomenon where current flowing through an object turns into heat energy to generate heat, and may be configured as, for example, a nichrome wire or any other suitable wire. The amount of heat generated by the wire rod increases or decreases depending not only on the magnitude of the current flowing through the wire rod, but also on the time during which the current flows therethrough.

The buttock heating element 41 is disposed in a back (rear) portion of an upper surface portion (seat portion) of the seat cushion part S1. The buttocks of the occupant A in the normal occupant posture are located immediately above the buttock heating element 41. The thigh heating element 42 is disposed in a near (front) portion of the upper surface portion (seat portion) of the seat cushion part S1. The thighs of the occupant A in the normal occupant posture are located immediately above the thigh heating element 42. The buttock heating element 41 and the thigh heating element 42 are positioned in the seat cushion part S1 to correspond to the respective parts of the occupant A in contact therewith. Thus, these heating elements serve as direct warmers configured to directly warm the occupant A.

On the other hand, the cushion side portion heating elements 43 are respectively disposed near right and left ends of the upper surface portion of the seat cushion part S1. If the occupant A is an adult having an average height and an average weight, and the occupant A is in the normal occupant posture, the thighs of the occupant A may be located between the right and left cushion side portion heating elements 43, or may be mostly located outside an area immediately above the cushion side portion heating elements 43. Thus, regions of the vehicle seat S near right and left ends of the upper surface portion of the seat cushion part S1 are not in contact with the occupant A. These regions each include the cushion side portion heating element 43. Thus, the cushion side portion heating elements 43 are spaced apart from the occupant A, and are radiant warmers configured to warm the occupant A by radiant heat.

The cushion front end portion heating element 44 is disposed near an upper end of a front surface portion of the seat cushion part S1. The cushion front end portion heating element 44 is elongated in the lateral direction, and located to correspond to portions of the occupant A near the back of his/her right and left knees of the occupant A. If the occupant A is in the normal occupant posture, portions of the occupant A below his/her thighs (e.g., the back of his/her knees) are spaced upward or forward apart from the cushion front end portion heating element 44. A region of the vehicle seat S near the upper end of the front surface portion of the seat cushion part S1 is not in contact with the occupant A. This region includes the cushion front end portion heating element 44. The cushion front end portion heating element 44 is spaced apart from the occupant A, and is a radiant warmer configured to warm the occupant A by radiant heat.

The amount of heat generated by each of the buttock heating element 41, the thigh heating element 42, the cushion side portion heating elements 43, and the cushion front end portion heating element 44 can be changed through a change in the current value, energization period, or any other factor controlled by the control unit 60. The output upper limit value of each of the buttock heating element 41, the thigh heating element 42, the cushion side portion heating elements 43, and the cushion front end portion heating element 44 (the upper limit of the amount of heat generated per unit time) is set by the control unit 60. The cushion side portion heating elements 43 and the cushion front end portion heating element 44 each has an output upper limit value lower than those of the buttock heating element 41 and the thigh heating element 42.

The waist heating element 45 is disposed in a lower portion of the front surface portion of the seat back part S2. The waist of the occupant A in the normal occupant posture is located immediately in front of this waist heating element 45. The waist heating element 45 is positioned to correspond to a region of the seat back part S2 in contact with the occupant A. Thus, this heating element serves as a direct warmer configured to directly warm the occupant A. The waist heating element 45 may warm the back. In this case, this heating element functions as a waist-and-back heating element, and is a direct warmer.

The respective shoulder side heating elements 46 are disposed near the right and left ends of an upper portion of the front surface portion of the seat back part S2, and are positioned so as to be prevented from reaching the back of the occupant A. If the occupant A is an adult having an average height and an average weight, and the occupant A is in the normal occupant posture, the left shoulder side heating element 46 is lateral to his/her left shoulder, and the right shoulder side heating element 46 is lateral to his/her right shoulder. Regions of the vehicle seat S near the right and left ends of the upper portion of the front surface portion of the seat back part S2 are not in contact with the occupant A. These regions each include the shoulder side heating element 46. The shoulder side heating elements 46 are spaced apart from the occupant A, and are radiant warmers configured to warm the occupant A by radiant heat.

The amount of heat generated by each of the waist heating element 45 and the shoulder side heating elements 46 can be changed through a change in the current value, energization period, or any other factor controlled by the control unit 60. The output upper limit value of each of the waist heating element 45 and the shoulder side heating elements 46 is set by the control unit 60. The waist heating element 45 has an output upper limit value lower than that of the shoulder side heating elements 46.

The turning on or off of the seat heater system 40 and the setting of the degree of heating of the seat heater system 40 can be achieved through an operation switch (not shown) or any other suitable switch in the cabin R, and can also be automatically controlled by the control unit 60.

(Configuration of Steering Heater 104a)

As shown in FIGS. 1 and 2, the steering heaters 104a are incorporated into respective portions of the steering wheel 104 in contact with the hands of the occupant A, specifically, portions of the steering wheel 104 gripped by the occupant A who is driving. Thus, the steering heaters 104a are positioned to correspond to regions of the steering wheel 104 in contact with the occupant A, and each serve as a direct warmer configured to directly warm the occupant A.

The steering heaters 104a may be each configured as a wire rod similar to that of each of the heating elements of the seat heater system 40, and are connected to, and controlled by, the control unit 60. The turning on or off of the steering heaters 104a and the degree of heating of the steering heaters 104a can be achieved through an operation switch (not shown) or any other suitable switch in the cabin R, and can also be automatically controlled by the control unit 60.

(Configuration of Foot Heater 30)

As shown by the phantom lines in FIGS. 1 and 2, the respective foot heaters 30 are arranged in a part facing the right calf of the occupant A and in a part facing the left calf of the occupant A. Specifically, the foot heaters 30 can be arranged in an interior material such as a door trim or a console. The foot heaters 30 are spaced apart from the occupant A, and are radiant warmers configured to warm the occupant A by radiant heat.

Each foot heater 30 may be configured as a wire rod similar to that of each of the heating elements of the seat heater system 40, and is connected to, and controlled by, the control unit 60. The turning on or off of each foot heater 30 and the setting of the degree of heating of the foot heater 30 can be achieved through an operation switch (not shown) or any other suitable switch in the cabin R, and can also be automatically controlled by the control unit 60.

(Configuration of Auxiliary Heater)

The buttock heating element 41, the thigh heating element 42, and the waist heating element 45 in the seat heater system 40, and the steering heaters 104a configure a direct warmer. The cushion side portion heating elements 43, the cushion front end portion heating element 44, and the shoulder side heating elements 46 in the seat heater system 40, and the foot heaters 30 configure a radiant warmer. In this embodiment, the cabin air-conditioning unit 10 is a main air conditioner, and the direct warmer and the radiant warmer are each an auxiliary heater that assists the main air conditioner. The direct warmer can be, for example, a heater or the like incorporated in an armrest. The radiant warmer can be, for example, a heater or the like incorporated in the lower surface of a steering column. Both the direct warmer and the radiant warmer can be provided, but only one of them may be provided. The auxiliary heater is not an essential component.

(Other Configuration of Vehicle Air Conditioner 2)

As shown in FIG. 3, the vehicle air conditioner 2 includes an outside air temperature sensor 71, an inside air temperature sensor 72, a humidity sensor 73, a solar radiation sensor 74, a temperature setting switch 75, a steering temperature sensor 76, a foot heater temperature sensor 77, a seat temperature sensor 78, a skin temperature sensor 79, and a pulse wave sensor 80. These sensors and the switch may be configured as members that have been known in the art, and are connected to the control unit 60 to output their sensed values in predetermined short cycles or successively, for example. The sensors that detect a temperature may include a thermocouple, for example.

The outside air temperature sensor 71 is disposed outside the cabin, and detects the air temperature outside the cabin. The inside air temperature sensor 72 is disposed inside the cabin R, detects the air temperature inside the cabin R, and can sense or estimate the temperature condition inside the cabin. The humidity sensor 73 is disposed inside the cabin R, detects the humidity inside the cabin R, and can sense or estimate the humidity condition inside the cabin. The solar radiation sensor 74 is disposed inside the cabin R, detects the amount of solar radiation entering the cabin R, and can sense or estimate the solar radiation condition inside the cabin R. The temperature setting switch 75 is disposed on the instrument panel 102 in the cabin R, and is used by the occupant A to set a desired conditioned air temperature.

The thermal environment around the occupant A in the cabin R includes the temperature condition inside the cabin R, the humidity condition inside the cabin R, and the solar radiation condition inside the cabin R. Among these three conditions, any one of them may be sensed or estimated, or other means may be adopted for detecting the thermal environment around the occupant A in the cabin R. Specifically, the thermal environment detector according to the present invention includes the inside air temperature sensor 72, the humidity sensor 73, and a solar radiation sensor 74, but at least one of them may be provided.

Further, while the seat heater system 40 is active, the temperature sensed by the seat temperature sensor 78 also represents the thermal environment around the occupant A in the cabin R. Further, while the foot heaters 30 are active, the temperature sensed by the foot heater temperature sensor 77 also represents the thermal environment around the occupant A in the cabin R. Further, while the steering heater 104a is active, the temperature sensed by the steering temperature sensor 76 also represents the thermal environment around the occupant A in the cabin R. Therefore, the seat temperature sensor 78, the foot heater temperature sensor 77, and the steering temperature sensor 76 may also serve as the thermal environment detector of the present invention.

The instrument panel 102 includes, not only the temperature setting switch 75, but also an on/off switch for air conditioning, an air volume adjusting switch, and an automatic air-conditioning switch, although not shown.

The steering temperature sensor 76 is disposed on the steering wheel 104, and detects the temperature of portions of the steering wheel 104 in contact with the occupant A, the temperature of the steering heaters 104a, and other temperatures. The foot heater temperature sensor 77 is disposed on the interior materials including the foot heaters 30, and detects the surface temperatures of the interior materials, the temperatures of the foot heaters 30, and other temperatures. The seat temperature sensor 78 is incorporated into the seat cushion part S1 and the seat back part S2 of the vehicle seat S, and detects the temperature of the skin material of each of the seat cushion part S1 and the seat back part S2 and the temperatures of the heating elements 41 to 46 of the seat heater system 40.

An infrared ray sensor that has been known in the art can be used as the skin temperature sensor 79. As shown in FIG. 1, by arranging the skin temperature sensor 79, for example, on a ceiling part and the like and orienting the direction of detection to the direction toward the occupant A, the intensity of infrared ray from each part of the occupant A can be detected, the skin temperature of the occupant A (the surface temperature of the occupant A) can be obtained based on the intensity of the infrared ray. To detect the intensity of infrared ray of a wide range, the skin temperature sensor 79 may be an infrared sensor capable of moving upward, downward, leftward, and rightward (scanning type), or include a plurality of infrared sensors. With the infrared sensor, an image based on the intensity of the infrared ray can be obtained. By subjecting this image based on the intensity of the infrared ray to image processing, not only it is possible to detect the surface temperature of each part of the occupant A, but also the position of each part of the occupant A and the physique of the occupant A can be estimated.

The skin temperature sensor 79 may be provided to each seat of the automobile 1, and may detect the skin temperature of each occupant. The skin temperature used in the later-mentioned control may be the skin temperature of the occupant on the driver's seat, or may be the skin temperature of an occupant in the rear seat. In a case in which the vehicle air conditioner 2 is capable of achieving zone air-conditioning, the skin temperature of an occupant in each zone can be detected and use the detected skin temperature in thermal control of the corresponding zone. The zone air-conditioning is, for example, air-conditioning such that an air-conditioned wind whose temperature is adjusted for a driver's seat side of the cabin R and an air-conditioned wind whose temperature is adjusted for the passenger's seat (the seat next to the driver's seat) of the cabin R are individually supplied, or air-conditioning such that an air-conditioned wind whose temperature is adjusted for a front seat side of the cabin R and an air-conditioned wind whose temperature is adjusted for the rear seat side of the cabin R are individually supplied. The configuration of the zone air-conditioning is well known.

The pulse wave sensor 80 is a sensor for detecting the pulse wave of the occupant A, and may be a traditionally known sensor. For example, the pulse wave sensor 80 may be an incorporated type that is incorporated in the seat cushion part S1 of the vehicle seat S as indicated by the broken line in FIG. 1. The pulse wave sensor 80 is a planar pressure sensor called smart rubber, and is capable of detecting, as a pulse wave, minute pressure fluctuations due to blood flow in the arteries in the buttocks and thighs of the occupant A. For example, the pulse wave sensor 80 may be one as disclosed in any of Japanese Unexamined Patent Publication Nos. 2009-132246, 2011-246037, 2011-24903, 2012-147925. Further, for example, the pulse wave sensor 80 may be a wristwatch type (wearable type) pulse wave detector, a millimeter wave radar type pulse wave detector which detects a pulse wave of the occupant A based on a reflection of a millimeter wave applied to the occupant A, or the like. Further, a technique to detect a pulse wave from arterioles of a fingertip (finger plethysmogram) may be adopted.

The pulse wave sensor 80 may be provided to each seat of the automobile 1, and may detect the pulse wave of each occupant. The pulse wave used in the later-mentioned control may be the pulse wave of the occupant on the driver's seat, or may be the pulse wave of an occupant in the rear seat. In a case in which the vehicle air conditioner 2 is capable of achieving zone air-conditioning, the pulse wave of an occupant in each zone can be detected and the detected pulse wave may be used in thermal control of the corresponding zone, provided that the skin temperature and the pulse wave for the control are of the same occupant A.

(Configuration of Control Unit 60)

Although not shown, the control unit 60 shown in FIG. 3 may be configured as, for example, a microcomputer including a central processing unit and a storage device (e.g., a ROM or a RAM) and may implement the later-described means and processes in the form of hardware or in the form of software (a program) stored in the storage device. The control unit 60 includes an operation state detection unit 61, an RRI detection unit 62, a comfort sensation calculation unit 63, an occupant thermal sensation calculation unit 64, and a target control value setting unit 65.

The control unit 60 is configured to perform automatic air conditioning control based on the values detected by the outside air temperature sensor 71, the inside air temperature sensor 72, the humidity sensor 73, and the solar radiation sensor 74, and the temperature set by the occupant A through the temperature setting switch 75, and any other elements. Specifically, if the outside air temperature and the temperature inside the cabin R are low, and heating is required, the cabin air-conditioning unit 10 is controlled to produce high-temperature air-conditioned wind. The produced wind is then supplied into the cabin R. At this moment, the required degree of heating is set based on the temperature set by the occupant A, the temperature in the cabin R, and other temperatures. The temperature and volume of the air-conditioned wind are adjusted in accordance with the degree of heating. In contrast, if cooling is required, the cabin air-conditioning unit 10 is controlled to produce low-temperature air-conditioned wind. The produced wind is then supplied into the cabin R. At this moment, the required degree of cooling is set based on the temperature set by the occupant A, the temperature in the cabin R, and other temperatures. The temperature and volume of the air-conditioned wind are adjusted in accordance with the degree of cooling. A technique for automatic air conditioning control has been known in the art. Thus, this technique will not be described in detail.

(Configuration of Operation State Detection Unit 62)

The operation state detection unit 62 is configured to detect the operation states of the cabin air-conditioning unit 10 and an auxiliary heater. The operation state of the cabin air-conditioning unit 10 includes, for example, on and off states and rotation rate of the blower motor 12*b*, an operation state of the air mix actuator 17, an operation state of the blowing direction switching actuator 18, an operation state of the refrigeration-cycle system 13, and the like. The rotation rate of the blower motor 12*b* can be detected by a voltage applied to the blower motor 12*b* or the like.

The operation state of the air mix actuator 17 means where the air mix actuator 17 positions the air mixing damper 15. By detecting the operation state of the air mix actuator 17, the current position of the air mixing damper 15 can be obtained. The position of the air mixing damper 15 can be expressed by an opening degree, that is, the opening degree of 100% may be the full hot state, and the opening degree of 0% may be a full cold state, or vice versa. The temperature of the generated air-conditioned wind can be estimated by experiment or the like.

The operation state of the blowing direction switching actuator 18 means which of the blowing modes the blowing direction switching actuator 18 has made the blowing direction switching dampers 16*a*, 16*b*, and 16*c* be in. By detecting the operation state of the blowing direction switching actuator 18, the current blowing mode can be obtained.

The operation state of the auxiliary heater means on and off states and the degree of heating of the buttock heating element 41, the thigh heating element 42, the cushion side portion heating elements 43, the cushion front end portion heating element 44, the waist heating element 45, and the shoulder side heating elements 46 in the seat heater system 40, the on and off states and the degree of heating of the steering heaters 104*a*, and on and off states and the degree of heating of the foot heaters 30.

(Configuration of RRI Detection Unit 62)

Figure 7:
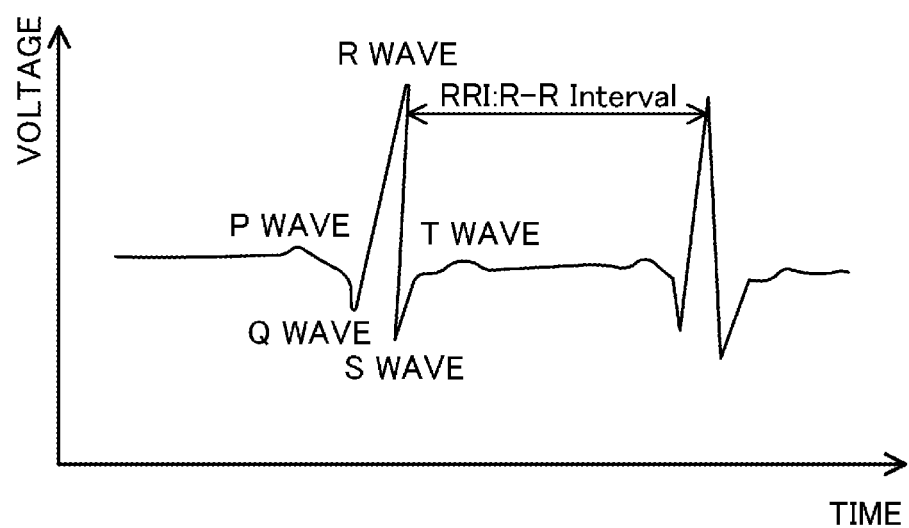
FIG. 7 is a graph illustrating an exemplary pulse wave.

The RRI detection unit 62 is an RRI detector for detecting an RRI from the pulse wave of the occupant A output from the pulse wave sensor 80. The pulse wave of the occupant A output from the pulse wave sensor 80, if properly detected, has a waveform as shown in FIG. 7, and RRI (R-R Interval) is a time interval between an R wave and another R wave. The method of detecting the time interval between the R waves may be a traditionally known method.

(Configuration of Comfort Sensation Calculation Unit 63)

The comfort sensation calculation unit 63 is a comfort sensation calculator that quantitatively calculates comfort sensation of the occupant A from the RRI detected by the RRI detection unit 62, and outputs a signal indicating the comfort sensation of the occupant A. In general, an RRI of a human is long when he or she is relaxed and short when he or she is stressed. Therefore, it is determined that the occupant A is uncomfortable if the RRI detected by the RRI detection unit 62 is shorter than a predetermined value within a predetermined time, and the occupant A is comfortable if the RRI is equal to or longer than the predetermined value within the predetermined time. An RRI threshold used to determine whether an occupant is uncomfortable or comfortable can be obtained by experiment or the like.

For example, where the RRI shorter than a predetermined value (uncomfortable) is "1" and the RRI equal to or greater than the predetermined value (comfortable) is "10", and where a fluctuation range of RRI is expressed in ten different levels, the comfort sensation and discomfort sensation can be quantitatively calculated according to the fluctuation range of the RRI, and the comfort sensation calculation unit 63 outputs a signal corresponding to 1 to 10. This is an example, and the comfort sensation may be expressed in three or five sensation levels, or in more than ten sensation levels.

(Configuration of Occupant Thermal Sensation Calculation Unit 64)

The occupant thermal sensation calculation unit 64 serves as an occupant thermal sensation calculator which obtains a thermal model of the occupant A based on thermal sensation calculation information containing a thermal environment around the occupant A detected by the inside air temperature sensor 72, the humidity sensor 73, the solar radiation sensor 74, the seat temperature sensor 78, the foot heater temperature sensor 77, the steering temperature sensor 76, and the like and an operation state of the cabin air-conditioning unit 10 detected by the operation state detection unit 61, quantitatively calculates the thermal sensation of the occupant A based on the thermal model, and then outputs a signal indicating the thermal sensation of the occupant according to the calculation result. The thermal sensation calculation information may contain the skin temperature of the occupant A detected by the skin temperature sensor 79.

The thermal sensation herein means feeling of hotness, coldness, and the like, which is a commonly used expression among people with ordinary skill in the art, as is elaborated, for example, on pages 33, 88 to 94 of "Car Air Conditioner" supervised by Kenichi Fujiwara, issued by Tokyo Denki University Press, on Sep. 20, 2009. The skin temperature is an example that well represents the thermal sensation. For example, there is an established technique of detecting a surface temperature of a thermal mannequin (thermal model) as the skin temperature, and based on this, evaluating the thermal sensation of the occupant A by giving 3 for "Hot", 2 for "warm", 1 for "slightly warm", 0 for "neutral (just about right)", −1 for "slightly cool", −2 for "cool", and −3 for "cold". The "high thermal sensation" means that the above numerical value is high and is on the hot side, whereas the "low thermal sensation" means that the above numerical value is low and is on the cold side. For example, where the horizontal axis represents the thermal sensation value as in the graph of FIG. 8, the "cold" is 1 and "hot" is 9. In this case, 5 represents "neutral (just right)".

If the temperature set by the occupant and the cabin temperature are substantially equal while the cabin air-conditioning unit 10 is performing heating, it is estimated that the interior of the cabin R is in a steady state. Thus, it can further be estimated that the thermal sensation of the occupant A is neither high nor low, that is, 5 on the horizontal axis in FIG. 8. On the other hand, if the cabin air-conditioning unit 10 is performing a strong heating, it is estimated that the interior of the cabin R is not yet warmed up. Thus, it can further be estimated that the thermal sensation of the occupant A is low, that is, 1 or 2 on the horizontal axis in FIG. 8. Further, if the temperatures detected by the seat temperature sensor 78, the foot heater temperature sensor 77, the steering temperature sensor 76, and the like are high, the amount of heat input to the occupant A is large. Thus, it can be estimated that the thermal sensation of the occupant A is high, that is, 8 or 9 on the horizontal axis in FIG. 8. The occupant thermal sensation calculation unit 64 combines these pieces of information with one another to comprehensively calculate and digitalize the thermal sensation and outputs the numerical value calculated.

When the thermal sensation calculation information contains information of skin temperature of the occupant A detected by the skin temperature sensor 79, the skin temperature of the occupant A is also used in the calculation of the thermal sensation. The skin temperature of the occupant A is usable as information indicating the thermal sensation of the occupant A, because it can be determined that the occupant A is feeling hot when the skin temperature of the occupant A is high, and determined that the occupant A is feeling cold when the skin temperature of the occupant A is low.

After the thermal model is obtained based on the thermal sensation calculation information containing the thermal environment around the occupant A and the operation state of the cabin air-conditioning unit 10, the skin temperature of the occupant A is compared with a corresponding part of the thermal model of the occupant A, and if the thermal sensation is determined as to be approximately the same, the thermal sensation of the occupant A is calculated based on the thermal model of the occupant A. On the other hand, if there is a difference beyond a predetermined range between the skin temperature of the occupant A and the corresponding part of the thermal model of the occupant A as a result of comparison, a correction coefficient is determined to bring the thermal model close to the thermal sensation based on the skin temperature of the occupant A, and the thermal model of the occupant A is corrected by using this correction coefficient. For example, the thermal model is corrected so that the higher the skin temperature of the occupant A, the greater the numerical value indicating the thermal sensation becomes, and that the lower the skin temperature of the occupant A, the smaller the numerical value indicating the thermal sensation becomes.

A thermal sensation calculation model for quantitatively estimating the thermal sensations may have been known in the art. For example, the calculation model can be the thermal sensation calculation model described in "Thermal sensation and comfort models for non-uniform and transient environments: Part I: Local sensation of individual body parts, Hui Zhang et al., Building and Environment 45, 2010, pp 380-388" or "thermal sensation and comfort models for non-uniform and transient environments, part Ill: Whole-body sensation and comfort Hui Zhang et al., Building and Environment 45 (2010) 399-410."

The model for calculating whether the occupant A feels comfortable can be a comfort sensation calculation model described in "Thermal sensation and comfort models for non-uniform and transient environments, part II: Local comfort of individual body parts Hui Zhang et al., Building and Environment 45 (2010) 389-398."

(Configuration of Target Control Value Setting Unit 65)
The target control value setting unit 65 serves as a target control value setter that sets a target control value of the cabin air-conditioning unit 10, based on a signal indicating the comfort sensation of the occupant A which is output from the comfort sensation calculation unit 63. When the signal indicates the comfort sensation is, for example, 8 or less out of ten, the target control value of the cabin air-conditioning unit 10 is set to strengthen the heating or cooling. The target control value is a target temperature or a target air volume of the air-conditioned wind.

When the signal indicates the comfort sensation is 8 or less out of ten, while heating is performed, the target control value is set so as to increase the temperature of the air-conditioned wind and the air volume of the air-conditioned wind. The target control value does not have to be constant, and the target control value during heating is set so that the temperature of the air-conditioned wind increases with a decrease in the numerical value indicating the comfort sensation (with an increase in the discomfort).

When the signal indicates the comfort sensation is 8 or less out of ten, while cooling is performed, the target control value is set so as to lower the temperature of the air-conditioned wind and increase the air volume of the air-conditioned wind. The target control value during cooling is set so that the temperature of the air-conditioned wind decreases with a decrease in the numerical value indicating the comfort sensation (with an increase in the discomfort).

The target control value setting unit 65 is configured to determine whether a signal from the comfort sensation calculation unit 63 and a signal from the occupant thermal sensation calculation unit 64 correspond to each other, and execute a process of correction for the signal output from the comfort sensation calculation unit 63, when both of the signals do not correspond to each other. This will be described later.

Figure 6:
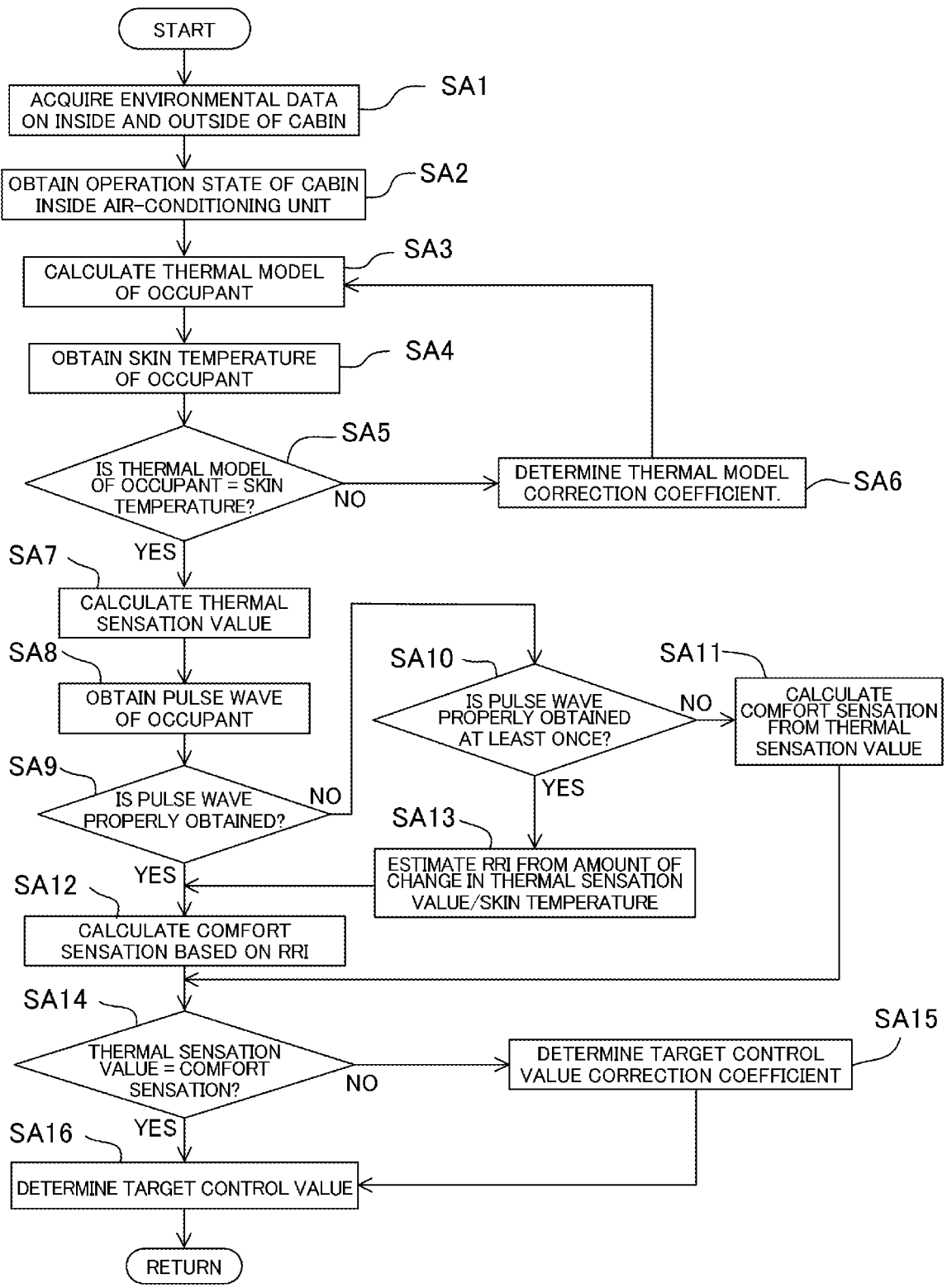
FIG. 6 is a flowchart illustrating control details of the vehicle air conditioner.

(Control Details by Control Unit 60)
Next, the control details by the control unit 60 will be described based on the flowcharts shown in FIG. 6. In step SA1 of the flowchart shown in FIG. 6, environmental data on the inside and outside of the cabin are acquired. The environmental data on the inside and outside of the cabin can be obtained from values detected by the outside air temperature sensor 71, the inside air temperature sensor 72, the humidity sensor 73, the solar radiation sensor 74, the steering temperature sensor 76, the foot heater temperature sensor 77, and the seat temperature sensor 78 and the state of the operation switches (such as the temperature setting switch 75). Then, in step SA2, the operation state of the cabin air-conditioning unit 10 is obtained. This operation state can be obtained from the operation state detection unit 61. The order of steps SA1 and SA2 is not limited, and steps SA1 and SA2 may be performed in parallel.

In step SA3, the thermal model of the occupant A is calculated. The thermal model of the occupant A can be obtained based on the thermal sensation calculation information containing the thermal environment around the occupant A and the operation state of the cabin air-conditioning unit 10. With the thermal model of the occupant A, the thermal sensation of each part of the occupant A can be obtained.

The following describes a case of acquiring the thermal sensation of each part of the occupant A. As shown in FIG. 2, the occupant A is virtually divided into a finite number of parts A1 to A16. The part A1 indicates the neck and head. The part A2 indicates a region from the chest to the abdomen, and the part A3 indicates a region from both the sides to the back and the waist. The part A4 indicates a region from the hypogastrium to the left and right thighs through the crotch. The part A5 indicates a region from the right shoulder to the right brachium, and the part A6 indicates a region from the left shoulder to the left brachium. The part A7 indicates a region from the vicinity of the right elbow to the right wrist, and the part A8 indicates a region from the left elbow to the left wrist. The part A9 indicates the right hand, and the part A10 indicates the left hand. The part A11 indicates a region from the right thigh to the right knee, and the part A12 indicates a region from the left thigh to the left knee. The part A13 indicates a region from the right shin to the right calf, and the part A14 indicates a region from the left shin to the left calf. The part A15 indicates a portion from the right ankle to the right toe, and the part A16 indicates a portion from the left ankle to the left toe. When the occupant A is virtually divided into parts, the number of the parts may be arbitrarily set, and the dividing boundary lines may be arbitrarily set.

In step SA4, the skin temperature of the occupant A is obtained. The skin temperature of the occupant A can be obtained from the detected value of the skin temperature sensor 79. The skin temperature of the occupant A may be an estimated value. In one preferred embodiment, the skin temperature of the occupant A is continuously obtained at least during the air-conditioning by the vehicle air conditioner 2.

In step SA5, whether the thermal model of the occupant A calculated in step SA3 is equal to the skin temperature of the occupant A obtained in step SA4 is determined. Although the thermal sensation can be obtained from the thermal model of the occupant A calculated in step SA3, the thermal sensation of the occupant A can also be obtained from the skin temperature of the occupant A in addition to the thermal model, as hereinabove described. In the determining process of step SA5, the thermal sensation obtained from the thermal model of the occupant A is compared with the thermal sensation obtained from the skin temperature of the occupant A. If these thermal sensations are substantially the same, it means that the thermal sensation obtained from the thermal model of the occupant A and the thermal sensation obtained from the skin temperature of the occupant A correspond to each other, and therefore, the determination is YES. On the other hand, in the determining process of step SA5, the thermal sensation obtained from the thermal model of the occupant A and the thermal sensation obtained from the skin temperature of the occupant A are different from each other, it means that the thermal sensation obtained from the thermal model of the occupant A and the thermal sensation obtained from the skin temperature of the occupant A do not correspond to each other, and therefore, the determination is NO.

If the determination is NO in step SA5, the operation proceeds to step SA6 to determine a thermal model correction coefficient for the occupant A. The determination of NO in step SA5 means that the thermal sensation obtained from the thermal model of the occupant A and the thermal sensation obtained from the skin temperature of the occupant A are different from each other, and in this case, the thermal model of the occupant A is corrected in step SA6 to bring the thermal sensation obtained from the thermal model of the occupant A into correspondence with the thermal sensation obtained from the skin temperature of the occupant A.

Therefore, when the thermal sensation obtained from the thermal model of the occupant A is lower than the thermal sensation obtained from the skin temperature of the occupant A, a correction coefficient that raises the thermal sensation obtained from the thermal model of the occupant A is determined so that the thermal sensation obtained from the thermal model of the occupant A becomes substantially the same as the thermal sensation obtained from the skin temperature of the occupant A. Therefore, when the thermal sensation obtained from the thermal model of the occupant A is higher than the thermal sensation obtained from the skin temperature of the occupant A, a correction coefficient that lowers the thermal sensation obtained from the thermal model of the occupant A is determined so that the thermal sensation obtained from the thermal model of the occupant A becomes substantially the same as the thermal sensation obtained from the skin temperature of the occupant A. This makes it possible to perform control prioritizing the thermal sensation obtained from the skin temperature of the occupant A.

After the thermal model correction coefficient for the occupant A is determined in step SA6, the operation returns to step SA3, and reflects the thermal model correction coefficient at the time of calculating the thermal model of the occupant A in step SA3. That is, in step SA3 for the first time after starting of the flow, the thermal model correction coefficient is not determined, and therefore, the thermal model is obtained based on the thermal sensation calculation information. However, for the second time and thereafter, if the thermal model correction coefficient is determined in step SA6, a process of reflecting that thermal model correction coefficient is performed. If the thermal model correction coefficient is not determined, a process of acquiring the thermal model based on the thermal sensation calculation information is performed.

Figure 8:
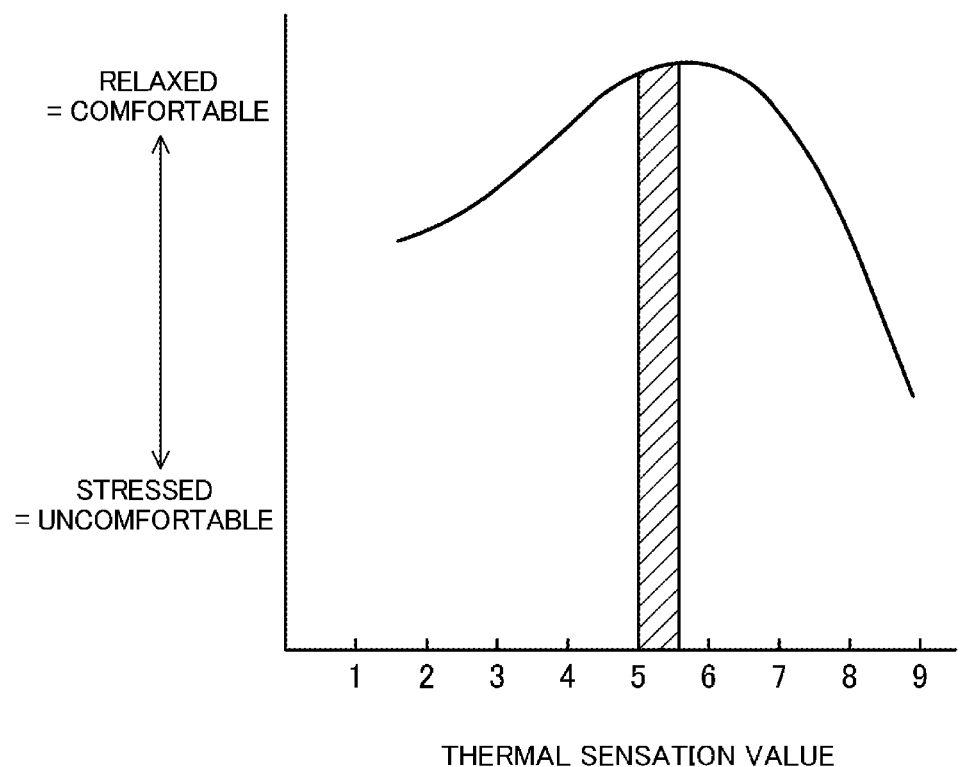
FIG. 8 is a graph illustrating a relationship between thermal sensation values and comfort sensation.

If the determination is YES in step SA5, and the operation proceeds to step SA7, a thermal sensation value is calculated. The thermal sensation value is calculated based on the thermal model of the occupant A calculated in step SA3. In this embodiment, as shown in the graph of FIG. 8, the thermal sensation value can be represented by a numerical value ranging from 1 on the cold side to 9 on the hot side.

In the subsequent step SA8, the pulse wave of the occupant A is obtained. The pulse wave of the occupant A can be obtained from the pulse wave sensor 80, and is continuously obtained at least during the air-conditioning by the vehicle air conditioner 2, in one preferred embodiment.

In step SA9, it is determined whether or not the pulse wave has been continuously obtained in step SA8. In the case of the automobile 1, the detection value of the pulse wave sensor 80 may be abnormal due to a disturbance factor, such as vibration during traveling, or contain a large amount of noise. In a case in which such a detection value is obtained it is determined that the pulse wave is not correctly obtained, and the determination is NO in step SA9. The operation then proceeds to step SA10. For example, in a case in which a state without any detection signal continues, or the detection signal is interrupted and does not have a waveform, or an abnormal waveform that is far different from a typical electrocardiographic waveform is detected, it is possible to determine that the pule wave has not been properly obtained.

In step SA10, it is determined whether or not the pulse wave is obtained at least once within a predetermined time. The predetermined time may be, for example, about 10 seconds to 30 seconds. If the pulse wave is obtained at least once in step SA10, the determination is YES, and the operation proceeds to step SA13, and the RRI is estimated from the thermal sensation value calculated in step SA7 and/or an amount of change in the skin temperature obtained in step SA4. When the thermal sensation value is 5, the RRI is estimated to be equal to or larger than a predetermined value (longer), and when the thermal sensation value is 1 or 9, the RRI is estimated to be shorter than the predetermined value. When the amount of change in the skin temperature per unit time is large, it is estimated that the fluctuation amount of RRI is large, and when the amount of change in the skin temperature per unit time is small, it is estimated that the fluctuation amount of RRI is small. The RRI may be estimated by combining the thermal sensation value calculated in step SA7 with the amount of change in the skin temperature obtained in step SA4.

If the pulse wave is not at all obtained, and the determination is NO in step SA10, the operation proceeds to step SA11 and the comfort sensation is calculated from the thermal sensation value calculated in step SA7. It is supposed that the thermal sensation value of 5 is comfortable, and the thermal sensation value of 1 or 9 is uncomfortable. The comfort sensation can be calculated to fall within any of the multiple levels between comfortable and uncomfortable, based on the thermal sensation value. That is, when the RRI is not detected by the RRI detection unit 62, the comfort sensation calculation unit 63 is able to calculate the comfort sensation of the occupant A based on the signal output from the occupant thermal sensation calculation unit 64.

If determination is YES in step SA9, the pulse wave is continuously and properly obtained. Therefore, in step SA12, the RRI is detected by the RRI detection unit 62, and the comfort sensation calculation unit 63 calculates the comfort sensation based on the detected RRI. Even when the RRI is estimated in step SA13, the operation proceeds to step SA12 and the comfort sensation calculation unit 63 calculates the comfort sensation based on the estimated RRI.

In step SA14, it is determined whether or not the thermal sensation value calculated in step SA7 and the comfort sensation calculated in step SA12 are equal to each other, or whether or not the thermal sensation value calculated in step SA7 and the comfort sensation calculated in step SA11 are equal to each other. That is, as shown in FIG. 8, the experiment results show a thermal sensation value equal to or close to 5 indicates a relaxed state (=comfortable), whereas a thermal sensation value close to 1 or 9 indicates a stressed state (=uncomfortable), and the comfort sensation and the thermal sensation value are co-related to each other.

If the thermal sensation value calculated in step SA7 and the comfort sensation calculated in steps SA11 and SA12 are substantially the same as a result of comparison, it means that the thermal sensation value calculated in step SA7 and the comfort sensation calculated in steps SA11 and SA12 correspond to each other, and the determination is YES. On the other hand, in the determining process in step SA14, if the thermal sensation value calculated in step SA7 and the comfort sensation calculated in steps SA11 and SA12 are different from each other as a result of comparison, it means that the thermal sensation value calculated in step SA7 and the comfort sensation calculated in steps SA11 and SA12 do not correspond to each other, and the determination is NO in step SA14.

If the determination is NO in step SA14, the operation proceeds to step SA15 to determine a target control value correction coefficient. The thermal sensation value calculated in step SA7 corresponds to the signal output from the occupant thermal sensation calculation unit 64. The comfort sensation calculated in step SA12 corresponds to the signal output from the comfort sensation calculation unit 53. The determination of NO in step SA14 means that the signal output from the occupant thermal sensation calculation unit 64 and the signal output from the comfort sensation calculation unit 53 do not correspond to each other. Therefore, in this case, the target control value correction coefficient is determined.

The target control value correction coefficient is a coefficient for correcting the signal output from the comfort sensation calculation unit 63, and is used in the process of step SA16 for determining the target control value. For example, in a case in which the reliability of an RRI obtained from the pulse wave of the occupant A is expected to be low due to vibration of the vehicle during traveling, the comfort sensation of the occupant A calculated by the comfort sensation calculation unit 63 may not be one that reflects the actual comfort sensation of the occupant A. On this account, the process of correction is performed to correct the signal output from the comfort sensation calculation unit 53 so that the signal from the occupant thermal sensation calculation unit 64 and the signal from the comfort sensation calculation unit 53 correspond to each other. The coefficient used in this process of correction is the above-mentioned target control value correction coefficient.

Since the target control value setting unit 65 corrects the signal output from the comfort sensation calculation unit 63 by using the target control value correction coefficient in step SA16, the thermal environment around the occupant A can be controlled without impairment of the comfort of the occupant A.

Meanwhile, if the determination is YES in the step SA14, the operation does not proceed to step SA15. Therefore, the target control value setting unit 65 disables the process of correction when it is determined that the signal output from the comfort sensation calculation unit 63 and the signal from the occupant thermal sensation calculation unit 64 correspond to each other.

Advantages of Embodiment

As hereinabove described, in the vehicle air conditioner 2 according to the present embodiment, the comfort sensation calculation unit 63 quantitatively calculates comfort sensation of an occupant A from an RRI of the occupant A, and a target control value of the vehicle air conditioner 2 is set based on the comfort sensation of the occupant A. Therefore, it is possible to achieve air conditioning control that reflects the comfort sensation of the occupant A, and improve the accuracy of the air conditioning control. Since the signal output from the comfort sensation calculation unit is corrected when the reliability of RRI of the occupant A is low, the thermal environment around the occupant A can be controlled without impairment of the comfort of the occupant A.

Other Embodiments

The embodiment described above is a mere example in every respect, and shall not be interpreted in a limited manner. Modifications or variations equivalent to the scope of claims fall within the scope of the present invention.

The comfort sensation calculation unit 63 may obtain the thermal environment around the occupant A by a thermal environment detector such as the inside air temperature sensor 72, the humidity sensor 73, and the solar radiation sensor 74, and obtain the operation state of the cabin air-conditioning unit 10, and when the RRI detected by the RRI detection unit 62 changes although the thermal environment around the occupant A and the operation state of the cabin air-conditioning unit 10 are not changed, calculate the comfort sensation of the occupant from the RRI before the change.

That is, the RRI changes due to a stress on the occupant A (due to a factor other than the thermal sensation). In this embodiment, when the RRI changes although there is no change in the thermal environment around the occupant A and the operation state of the cabin air-conditioning unit 10, it is estimated that the RRI has changed due to a factor other than the thermal sensation, and the comfort sensation of the occupant A is calculated from the RRI before the change.

Therefore, the accuracy of calculating the comfort sensation of the occupant A is improved.

Further, the comfort sensation calculation unit 63 may obtain the thermal environment around the occupant A by a thermal environment detector such as the inside air temperature sensor 72, the humidity sensor 73, and the solar radiation sensor 74, obtain the operation state of the cabin air-conditioning unit 10 and the skin temperature detected by the skin temperature sensor 79, and when the RRI detected by the RRI detection unit 62 changes although there is no change in the thermal environment around the occupant A, the operation state of the cabin air-conditioning unit 10, and the skin temperature of the occupant A, calculate the comfort sensation of the occupant from the RRI before the change.

In this embodiment, when the RRI changes even though there is no change in the thermal environment around the occupant A, the operation state of the cabin air-conditioning unit 10, and the skin temperature of the occupant A, it is estimated that the RRI has changed due to a factor other than the thermal sensation, and the comfort sensation of the occupant A is calculated from the RRI before the change. Therefore, the accuracy of calculating the comfort sensation of the occupant A is improved.

As can be seen from the foregoing description, the present invention is useful for a vehicle air conditioner for an automobile or any other vehicle, for example.

What is claimed is:

1. A vehicle air conditioner mounted on a vehicle, comprising:
    thermal environment detector configured to detect a thermal environment around an occupant in a cabin;
    an R-R Interval detector configured to detect an RRI from a pulse wave of the occupant;
    a comfort sensation calculator configured to calculate comfort sensation of the occupant from the RRI detected by the RRI detector, and output a signal indicating the comfort sensation of the occupant;
    a thermal environment control device configured to control the thermal environment around the occupant;
    a target control value setter configured to set a target control value of the thermal environment control device, based on the signal output from the comfort sensation calculator, which indicates the comfort sensation of the occupant; and
    an occupant thermal sensation calculator configured to obtain a thermal model of the occupant based on thermal sensation calculation information containing the thermal environment around the occupant which is detected by the thermal environment detector and an operation state of the thermal environment control device, calculate thermal sensation of the occupant, and output a signal indicating the calculated thermal sensation, wherein
    the target control value setter is configured to determine whether the signal from the comfort sensation calculator and the signal from the occupant thermal sensation calculator correspond to each other, and execute a process of correction for the signal output from the comfort sensation calculator, when both of the signals do not correspond to each other.

2. The vehicle air conditioner of claim 1, wherein
    the target control value setter is configured to disable the process of correction when it is determined that the signal output from the comfort sensation calculator and the signal output from the occupant thermal sensation calculator correspond to each other.

3. The vehicle air conditioner of claim 1, further comprising:
    a skin temperature detector configured to detect a skin temperature of the occupant,
    wherein the thermal sensation calculation information contains the skin temperature of the occupant detected by the skin temperature detector.

4. The vehicle air conditioner of claim 1, wherein
    the comfort sensation calculator is configured to obtain the thermal environment around the occupant detected by the thermal environment detector and the operation state of the thermal environment control device, and when the RRI detected by the RRI detector changes although the thermal environment around the occupant and the operation state are not changed, calculate the comfort sensation of the occupant based on the RRI before the change.

5. The vehicle air conditioner of claim 3, wherein
    the comfort sensation calculator is configured to obtain the thermal environment around the occupant detected by the thermal environment detector, the operation state of the thermal environment control device, and the skin temperature detected by the skin temperature detector, and when the RRI detected by the RRI detector changes although the thermal environment around the occupant, the operation state, and the skin temperature of the occupant are not changed, calculate the comfort sensation of the occupant based on the RRI before the change.

6. The vehicle air conditioner of claim 1, wherein
    when the RRI cannot be detected by the RRI detector, the comfort sensation calculator calculates the comfort sensation of the occupant based on the signal output from the occupant thermal sensation calculator.

7. A vehicle comprising the vehicle air conditioner of claim 1.

* * * * *